(12) United States Patent
Strachan

(10) Patent No.: US 6,811,564 B1
(45) Date of Patent: Nov. 2, 2004

(54) MOLECULAR RESONANCE STIMULATED BY LOW INTENSITY LASER LIGHT

(75) Inventor: John Scott Strachan, Edinburgh (GB)

(73) Assignee: Todd Ovokaitys, Del Mar, CA (US)

(*) Notice: Subject to any disclaimer, the term of this patent is extended or adjusted under 35 U.S.C. 154(b) by 110 days.

(21) Appl. No.: 10/069,052

(22) PCT Filed: Aug. 29, 2000

(86) PCT No.: PCT/GB00/03280
§ 371 (c)(1),
(2), (4) Date: Feb. 21, 2002

(87) PCT Pub. No.: WO02/02187
PCT Pub. Date: Jan. 10, 2002

(30) Foreign Application Priority Data

Aug. 28, 1999 (GB) ............................................. 9920351

(51) Int. Cl.⁷ ................................................ A61N 1/00
(52) U.S. Cl. ................................ 607/89; 606/3; 606/10
(58) Field of Search .......................... 607/88–93; 606/3, 606/10–13

(56) References Cited

U.S. PATENT DOCUMENTS

| | | | |
|---|---|---|---|
| 4,536,883 A | 8/1985 | Chapline, Jr. | |
| 4,834,474 A | 5/1989 | George et al. | |
| 4,951,663 A | * 8/1990 | L'Esperance, Jr. | ........... 607/89 |
| 5,288,995 A | * 2/1994 | Strachan | ................ 250/227.21 |
| 5,658,234 A | 8/1997 | Dunlavy | |
| 6,064,500 A | * 5/2000 | Strachan | ..................... 359/569 |

FOREIGN PATENT DOCUMENTS

WO            97/22022        6/1997

* cited by examiner

*Primary Examiner*—David M. Shay
(74) *Attorney, Agent, or Firm*—Bateman IP Law Group

(57) ABSTRACT

This invention provides an apparatus comprising a laser diode (2) whose wavelength is modulated by an amplitude modulator (1). The laser output is collimated by a lens (3) and passed through an optical element (4) which contains two diffraction gratings spaced by a refractive element. The resulting output contains an interference pattern which can be selected and controlled to interact with chosen molecules so as to induce molecular resonance.

13 Claims, 7 Drawing Sheets

MOLECULAR RESONANCE STIMULATED BY LOW INTENSITY LASER LIGHT

This application is the US national phase application of PCT International Application No PCT/GB00/03280 filed Aug. 29, 2000.

The present invention relates to molecular resonance of molecules, in particular molecular resonance generated by laser radiation.

The concept of introducing high Q molecules that may be stimulated by laser light to deliver toxic or therapeutic effects is known from Dunlavy U.S. Pat. No. 5,313,315. However, the direct stimulation of natural biological processes by means of molecular resonance using modulated or selective wavelength lasers has hitherto proved to be impossible. This is because of the scattering nature of the medium, the close proximity of many resonances in natural molecules and the difficulty of differentially raising the temperature and thereby the reactivity of individual desired molecules.

The present invention defines an apparatus and method which overcomes some of these problems and covers the nature and type of molecule susceptible to differential stimulation.

Many critical chemical reactions in the body are functions of the Cell Surface Cell Adhesion Molecules that are in turn morderated by various integrins. The geometric structure of many Cell Adhesion Molecules and particular integrins is such that they are capable of supporting a resonance at relatively low frequency and surprisingly high Q. Unlike most protein structures which are heavily damped or inherently rigid in structure these molecules generally take the form of a pair of relatively rigid structures separated by space often bridged by a single strand. This structure is especially sensitive to periodic stimulation by a laser source especially when the molecule surface is neutral or slightly negatively charged. The polar and hydrophobic regions of the molecule also differentially absorb energy from laser light. This causes brief alterations in both the structural bond energy and consequently tends to amplify the vibration of the molecule. The effect of this is to slightly increase the chemical reactivity of particular molecules on a cell surface relative to the surrounding molecules of a more generally damped structure or other high Q molecules of a different resonant frequency.

In vivo the scattering of light at suitable excitation wavelengths is extreme and as a result even quite low frequency modulation signals tend to be corrupted by the multiple scatter path lengths and by the delay in absorption and release of photons in those atoms at low energy states.

Also if continuous laser radiation is delivered to a mass of cells the high damping factor of the structure means that in general the overall temperature of the cell mass rises. This occurs even if modulated at the resonant frequency of a particular molecule. The use of laser radiation in this way produces an increase in the reactivity of the entire cell surface which means that no actual change in the reaction products occur because the cells are in general, at equilibrium.

Conversely if very low energy is delivered at the resonance frequency of the cell adhesion molecules or if energy can be delivered as an intermittent pulse of extremely short duration, the cell adhesion molecules and the integrins with their inherently high Q structure tend to maintain a slightly higher temperature than the surrounding molecules. Thus the cell adhesion molecules can be stimulated to a greater reactivity than the surrounding surface molecules.

Many biological processes can be disturbed into a cascade of increasing reactivity if an initial response is initiated. The immune response is a powerful example of this but the nature of biological reactions on the cell surface means that similar cascade reactions occur for a wide variety of initial conditions disturbed from equilibrium. Thus a very small change in the reactivity of a surface molecule for a short time can result in a dramatic change in the chemistry of the cell surface for a considerable period after the stimulation.

This effect depends on the cell chemistry being substantially in equilibrium at the commencement of the delivery of the radiation, otherwise the resonance effect will tend to be swamped by the current dominant reaction. Thus the target cells must be in a relatively neutral pH environment and obviously not engaged in a vigorous metabolic process. Ideally also the cell surface molecule would be neutral or slightly negative as this increases the absorption of photons and so increases the transfer of energy from the laser to the molecule.

Although this limits the use of this method, it has one beneficial effect with respect to therapeutic use in carcinomas. The undifferentiated cells of a carcinoma are generally at equilibrium on the surface as most of the chemical energy of the cell is expended internally in the cell duplication process. This means that the undifferentiated cells of a carcinoma are particularly susceptible to the effect of the method on the surface chemistry since by their nature they conform to the ideal requirements for low energy disturbance of the equilibrium.

It is a critical requirement of this effect that the initial stimulation is periodic and of very low overall energy, as higher energy stimulation would merely raise the temperature of the entire cell by conduction and would not change the reaction equilibrium. To achieve such a change, individual molecules on the cell surface must be at different temperatures. Ideally it would consist of small, directed bursts of light modulated at the frequency of the desired molecule. Unfortunately it is clearly imposbible to direct such a beam in the highly scattering medium of a living human body.

If a conventional laser or simple light beam is directed at a highly-scattering medium, the modulation is eliminated at any substantial frequency because the light paths to any given point are so numerous and of such differing lengths that any modulation is reduced to noise after a few millimetres of the scattering medium. Even at lower frequencies the general level of overall energy delivered to the cells means that conduction and convection tend to raise the overall temperature of the cell surface rather than allow isolated temperature differences to exist for any useful length of time. Further it is impractical to generate a light pulse which is of sufficiently short duration and with a sufficiently high pulse repetition frequency to be of practical use in the stimulation of any resonance of a Q likely to occur in a living cell surface molecule.

This invention provides a means of differentially stimulating at least those molecules susceptible by their structure to resonant stimulus.

The invention and preferred features thereof are defined in the appended claims.

Embodiments of the invention will now be described, by way of example only, with reference to the drawings, in which.

Figure 1:
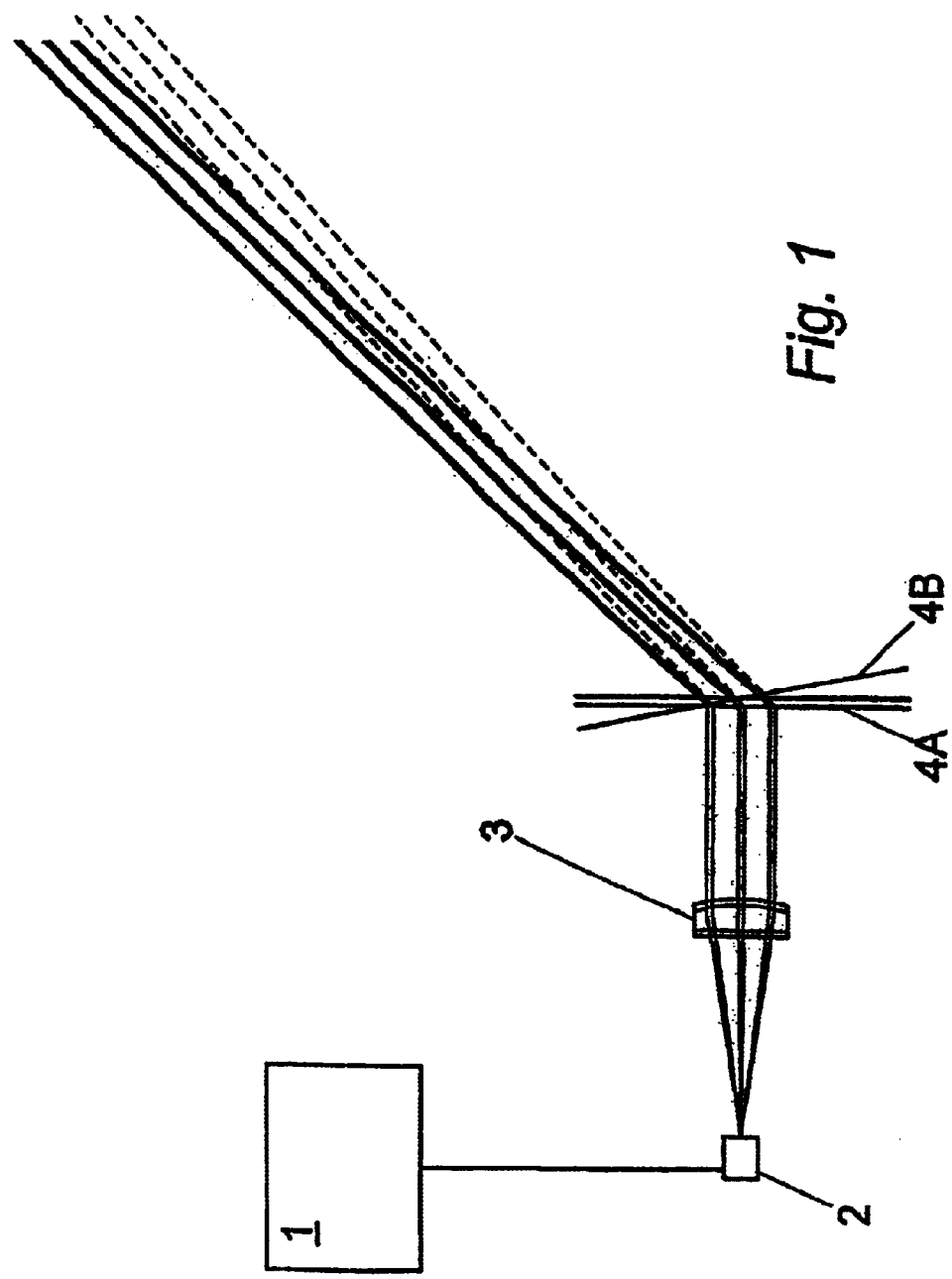
FIG. 1 is a block diagram of an apparatus embodying the invention.

Referring to FIG. 1, the apparatus comprises a laser diode 2 which is controlled by an amplitude modulator 1. The laser diode 2 is selected to have a, reasonably linear relationship between current and wavelength with minimum mode hopping. The amplitude modulator 1 modulates the current to the laser diode which in turn results in a very small wavelength modulation of the laser, for purposes discussed below.

Figure 2:
FIG. 2 illustrates an interference pattern produced by the apparatus of FIG. 1.
Figure 3:
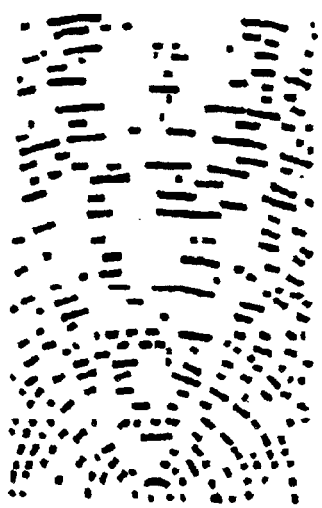
FIG. 3 shows the same interference in a scattering medium.
Figure 4:
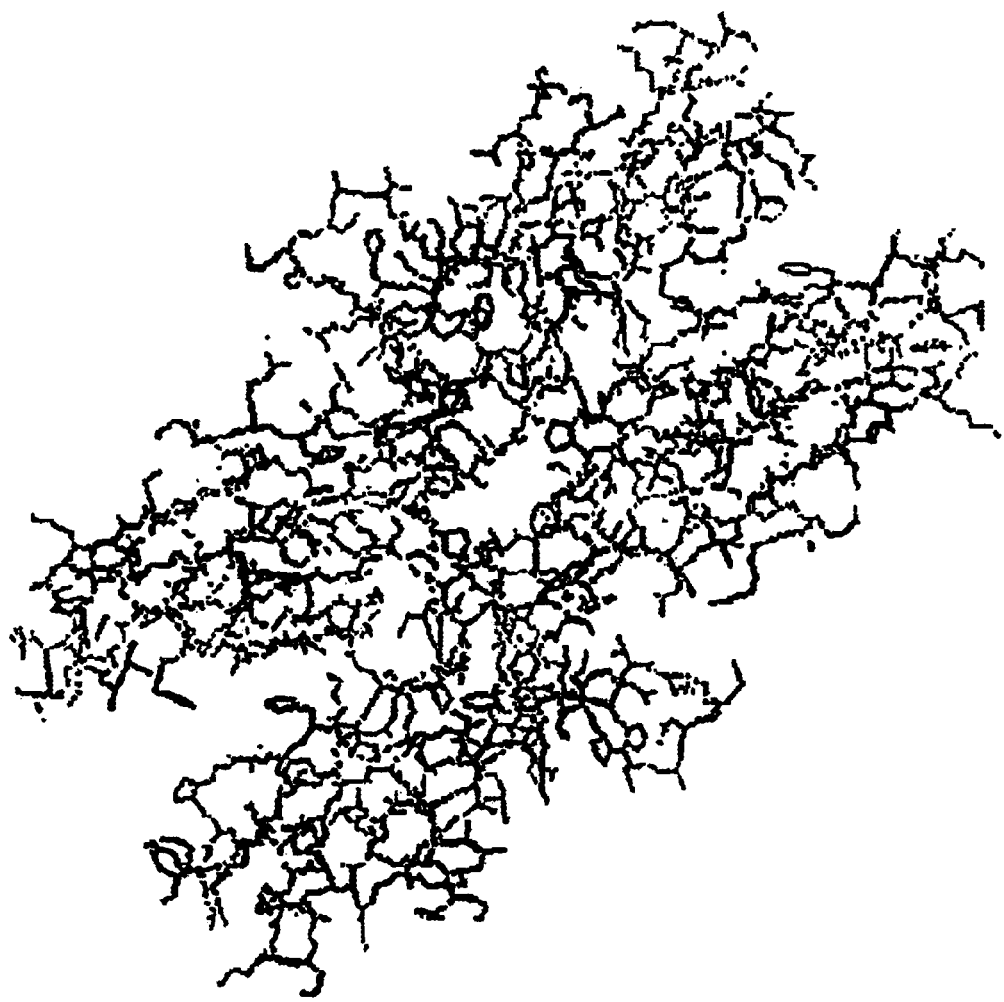
FIGS. 4 and 5 show typical cell adhesion molecules.
Figure 5:
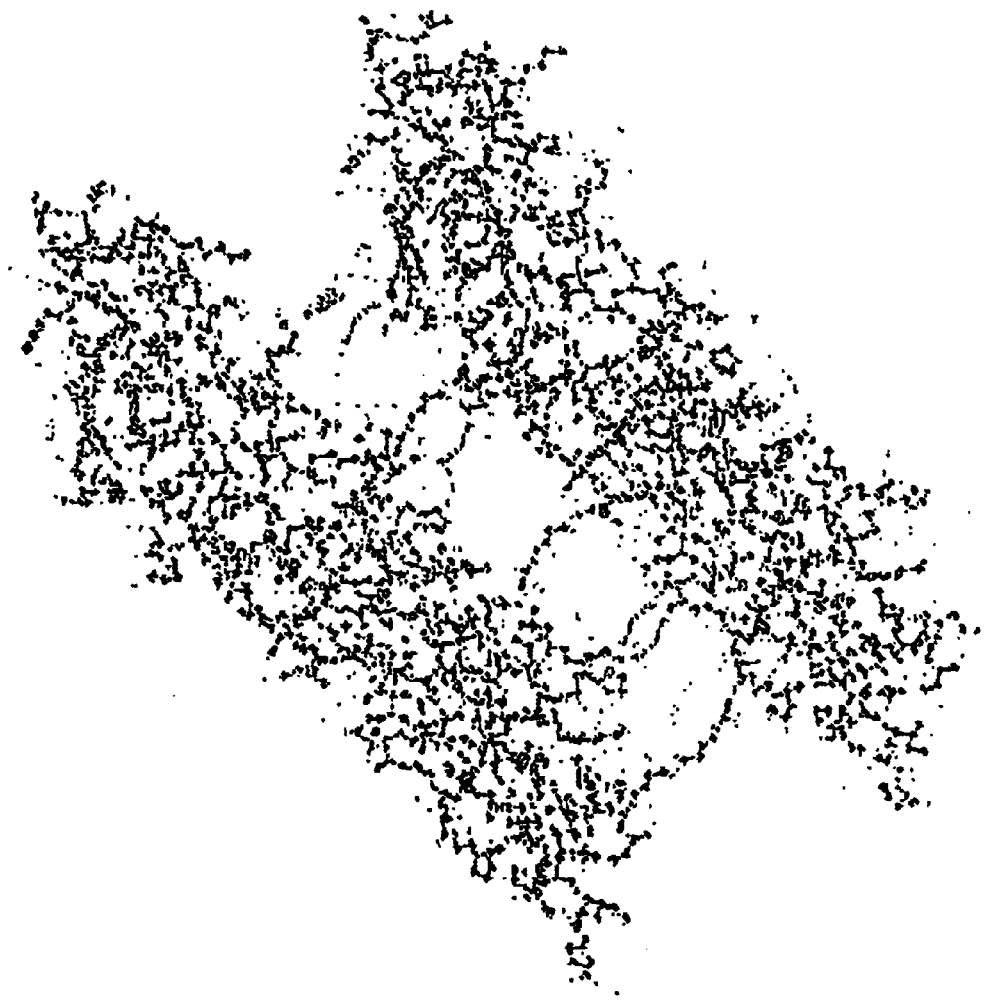
Figure 6:
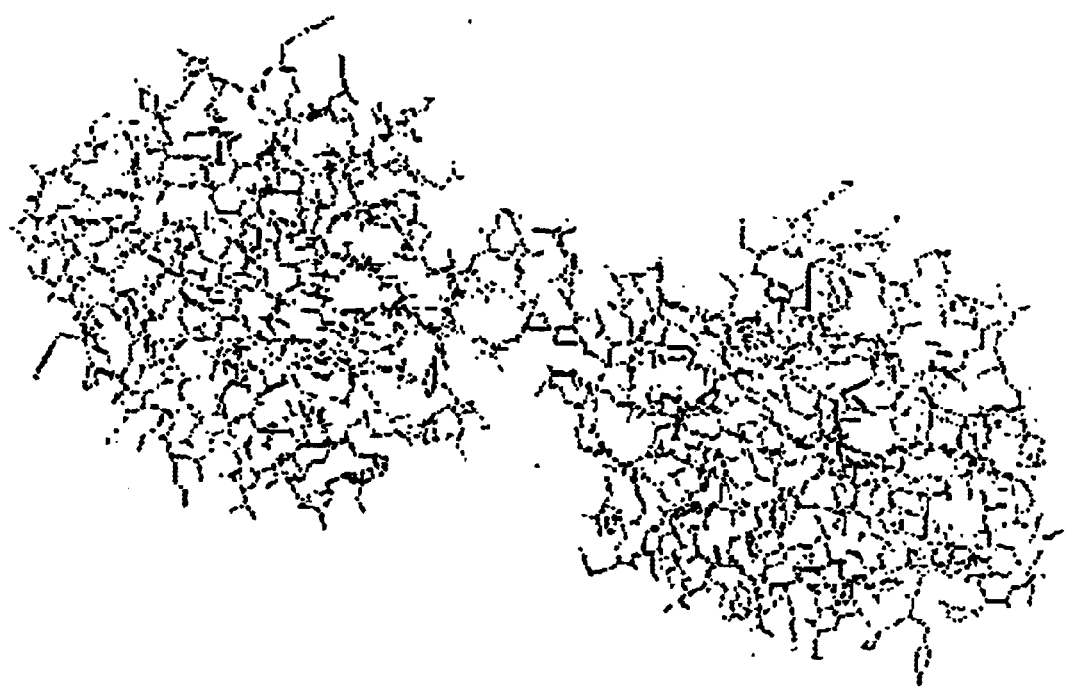
FIG. 6 shows a human integrin molecule with a single substantial high Q resonance.
Figure 7:
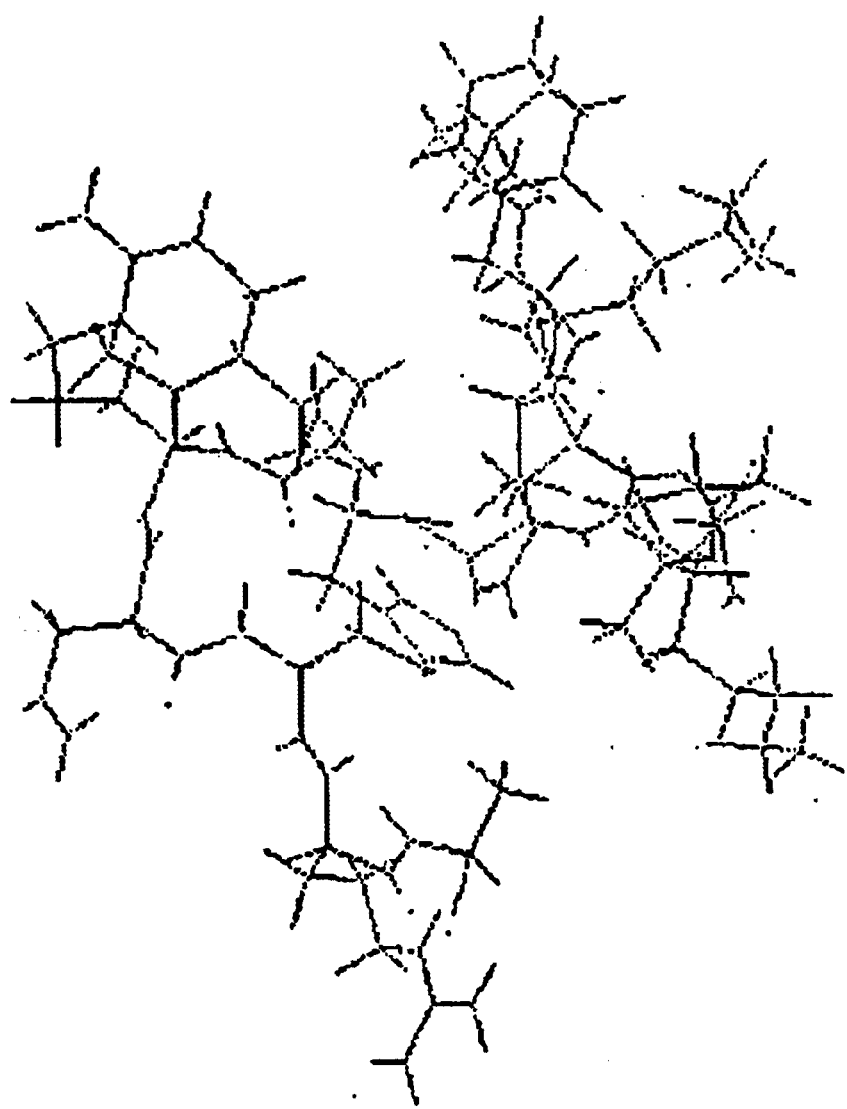
FIG. 7 shows the zinc structure of the GAG protein in the HIV virus.
Figure 8:
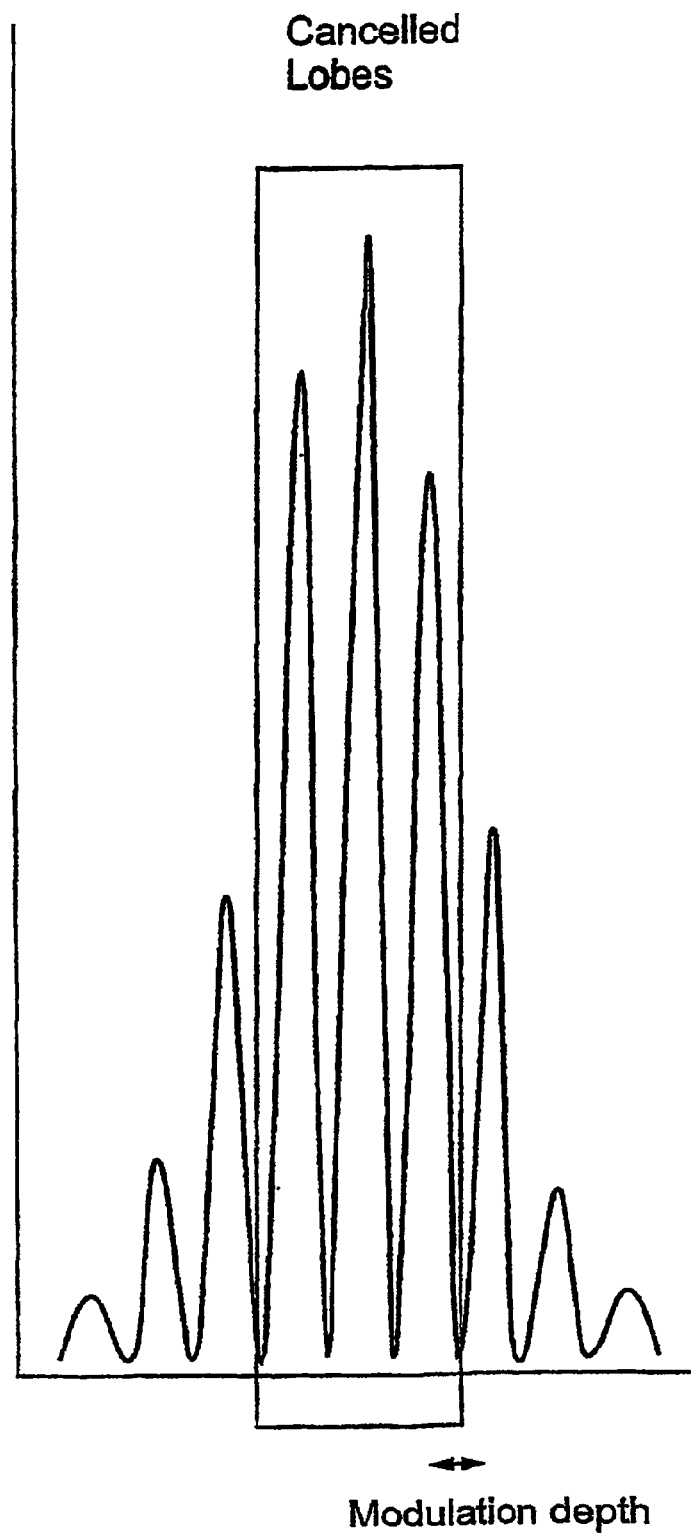
FIG. 8 shows a typical laser diode spectrum.

The output of the laser diode 2 is collimated by a lens 3 and passed to an optical element 4. The optical element 4 consists of a first diffraction grating, a refractive element, and a second diffraction grating such that the beam is substantially cancelled. A preferred form of the optical element 4 is as disclosed in WO97/22022 (now EP-A1-0865618A and U.S. Pat. No. 6,064,500). This allows the cancellation to occur over a small percentage of the wavelength variance of the laser source, rather than at a single critical wavelength. Wavelengths beyond the acceptance bandwidth of the cancelling optic 4 above and below the centre frequency pass without being cancelled. This means that a complex Fresnel/Fraunhoffer zone will be generated, defined by the beat frequency of the high and low frequencies as a function of the aperture. This means that relatively sparse zones of constructive interference will occur between the high and low frequency passes of the cancellation element in selected directions from the aperture, as shown in FIG. 2.

As seen in FIG. 1, the optical element can be adjusted angularly between positions 4A and 4B. This varies the ratio of constructive to destructive interference.

In effect the continuous beam is transformed into a string of extremely short duration pulses typically of sub femto second duration. The small wavelength modulation of the laser diode 2 caused the constructive and destructive nodes to move rapidly through the volume of the Fresnel zone of the collimator lens aperture. This has the effect of similating very short (sub picosecond) pulse behaviour at any point in the Fresnel zone through which the nodes pass at a pulse repetition frequency defined by the amplitude modulator frequency.

The wavelength of the cancellation and constructive interference zones for a theoretical single path would be the difference between the two frequencies. If the bandwidth of the cancelling element is narrow this difference is very small and the effective wavelength of the cancelled/non-cancelled cycle would be very long, of the order of pico-seconds. Therefore, the system would behave substantially similarly to a system with no cancellation because it requires an aperture much larger than the primary light wavelength to generate a useful Fresnel/Fraunhoffer zone. Such an aperture would greatly multiply the available Feynman diagram paths eliminating any useful effect, even if it were possible to generate a sufficiently coherent source of such an aperture.

If the beat frequency can be made high enough the wavelength of the cancelled to non-cancelled cycle can be a fraction of a practical aperture. This will make this wavelength sufficiently small to limit the Feynman paths to within a cycle or two in free space allowing the Fresnel/Fraunhoffer effect to be apparent. Since the centre frequency and spectrum spread of a laser diode is easily modulated by adjusting the current and or temperature of the junction, the pattern of the Fresnel/Fraunhoffer zones can be varied dramatically by very small variations in the wavelength of one or both pass frequencies. Such modulation is produced in the apparatus of FIG. 1 by the amplitude modulator 2.

Ideally the diode is modulated only slightly so that the frequencies of the laser spectra move by an amount smaller than that which would cause a second lobe to spill outside the bandpass of the cancellation element. As described above the aperture of the apparatus has a dimension some substantial multiple of the wavelength of the laser and some significantly smaller multiple of the cancellation cycle. Thus the number of different Feynman diagram path lengths will be substantially less than infinite for any given cycle length. Thus as different rays from the laser take slightly different paths through the optical element and thereafter cause the complex Fraunhoffer zone within the beam the pattern generated is the inverse of a typical narrow spectrum Fraunhoffer zone.

Therefore, instead of the centre frequencies of the beam being in general uncancelled, the centre frequencies are totally cancelled. Thus instead of a general constant level:of light in the beam, the beat frequency beam is characterised by isolated relatively sparse "islands" of constructive interference occurring in the generally cancelled beam. Small variations in the centre frequency of the laser as a result of modulation of the current or temperature of the diode cause these islands of constructive interference to move rapidly within the beam.

Thus at any given point within the beam path, a constructive interference node can be made to modulate with respect to the modulation frequency of the laser, irrespective of the scattering of the path to that point. This is because few areas of constructive interference exist in the initial beam and while a constructive node can occur at any point which happens to have suitable path lengths through the scattering medium to the source, the initially cancelled portion of the beam can not be reconstructed to become a constructive node at any point. Since the modulation of the laser changes the locations of the constructive nodes at the modulation frequency of the laser the result is that for any point (or more accurately for the substantial majority of points) within the beam a modulation occurs irrespective of the scattering nature of the medium. This is because the probability of a scatter from one sparse node to a region where another sparse node has existed within frequency of the modulation is extremely low.

In a typical coherent beam, the presence of constructive or destructive interference is of equal likelihood aid the modulation of the beam will generally shift one constructive node only to be replaced by another causing any initial modulation of the beam to swamped by the noise of the multiple paths. In contrast, the limiting factor for the modulation frequency of a sparse constructive interference beam is simply that the overall maximum path length of any substantial probability in the Feynman diagram. Path length is substantially shorter than the wavelength of the modulation.

For a depth of five or six centimetres in human tissue this allows frequencies in excess of 10 MHz to be successfully modulated and in many human tissues such as bone or neural tissue the depth would be substantially greater or the limiting frequency higher.

A conventional coherent or incoherent beam would have high probability paths in the Feynman diagram. These paths would overlap at very low frequencies (kHz) and be of little practical use in the stimulation of molecular resonance. It should be noted however that the phenomena described above may be used as a means to multiply the modulation frequency, up to the point where the beam effectively becomes continuous. Thus by careful selection of the aperture, the region of the beam selected for transmission through the medium and the modulation frequency it impossible to cause the constructive nodes to pass across any given point in the beam at frequencies many times higher than the modulation frequency. In ideal conditions the duration of exposure to a constructive node of any point would be for a period equivalent to a quarter of the duration of a wavelength of the molecular frequency repeated once per cycle.

If the wavelength of the laser is chosen to be one easily absorbed by the atomic structures it is desired to induce to resonance, then the beam will efficiently deliver the desired modulation frequency a to the desired molecules. The energy of the beam is extremely low but sufficiently high to differentially raise the temperature of those molecules of sufficient Q. Higher energy intensity would tend to cause sufficient scatter even from the isolated island nodes to swamp the modulation. Again the result would be a general temperature increase rather than the differential temperature increase of the desired molecules.

Higher intensity can not significantly increase the energy delivered to the desired molecules. Once the probability of a single photon absorption at any point on the molecule in a given and resonant frequency cycle is exceeded, there little advantage in increasing the intensity since a second photon will scatter without delivering more energy to the given atom structure. The maximum temperature difference that can be induced will be a function of the damping factor and the Q of the resonant component of the molecule. Therefore, increasing the time of stimulation is pointless beyond some reasonable multiple of the known time required to initiate the reaction desired because the maximum possible temperature variance will occur within a few seconds.

The effect is therefore, only of merit in systems where a small temperature variance can disturb the equilibrium. Naturally this limits the range of molecules that can be stimulated by this method. It is fortunate however that many of the most usefully stimulated molecules have exactly the characteristics required. Most particularly the cell adhesion molecules and integrins mentioned above. It should be noted of course that all biological reactions occur within a narrow temperature range and the progress of most reactions can be varied quite significantly by small temperature differences. It is of course a natural consequence of light stimulation of a molecular resonance that the molecular node temperature of the resonant structure will coincide with the maximum valence state of the atoms since they are in the process of absorbing and emitting photons and so the electrons are in general at a relatively high energy state. Naturally specific photochemical reactions will be favoured and this may either help or hinder the ability of the method to stimulate a specific desired reaction depending on the proximity of unwanted photochemical reaction sites to the resonant stimulated sites. In designing a specific stimulus these factors should be taken into account along with the equilibrium state and the pH.

As stated above cell adhesion molecules and human integrins such as Alpha 4 Beta 1 are ideally suited for excitation to chemical activity by this method.

The stimulation of cell adhesion molecules and integrins moderates a number of extremely useful biological processes. Not least of these is cell adhesion itself. It is obviously beneficial to stimulate the adhesion molecules of a carcinoma as the cell adhesion of carcinomas is relatively depressed and enhancing the adhesion serves to reduce the probability of metastasis. Such an effect would be especially beneficial prior to the excision of a tumour, reducing the likelihood of surgically shedding carcinoma cells into the blood or lymph system. The cell adhesion process and the integrins especially Alpha 4 Beta 1 and Alpha 4 Beta 2 are responsible not only for adhesion but also cell recognition.

Bissel and Weaver have shown that by chemical inhibition of adhesion sites of Alpha 4 Beta 1, the cell recognition can be moderated. It is therefore possible to reduce an undifferentiated carcinoma cell to its phenotype by correctly moderating the adhesion reaction. The method used by Bissel and Weaver is practical for in vitro application and can be used as described in their patent for the measurement of response to chemotherapy but it can not practically be used in vivo. Conversely the laser radiation method can be used in vivo and because of the extremely low energies it is inherently safe at least in terms of the radiation used. Care must of course be taken to ensure that the stimulation delivered will have a desirable consequence and much work is needed to determine both the chemical responses that are most easily stimulated and which of those are desirable in a given case.

Gradually a library of reaction responses susceptible to the stimulation will be developed from theory and experiment and this library will be used to define a range of reactions that are both of clinical use and practical to stimulate. To date we have demonstrated the stimulation of adhesion in leukocytes and neural carcinomas. We have demonstrated substantial moderation of cell surface chemistry in the prostate gland.

This shows promise in the treatment of various carcinomas. Stimulation of cell adhesion and recognition alters the metabolism of the carcinoma and causes induced, spontaneous apoptosis as a result of undifferentiated cells communicating sufficiently. This in turn causes the natural apoptosis of undifferentiated cells in an undifferentiated environment. We have substantial evidence that like Bissel and Weaver we have observed the reduction to phenotype of undifferentiated cells and leukocytes. Wayner U.S. Pat. No. 5,730,978 has shown an integrin-moderated process which suggests that the method may have application in the treatment of autoimmune diseases and in the manipulation of the immune response in general.

In vitro, the method can be used to alter the chemistry of a variety of proteins and simple amino acid structures in a manner that may be useful in the production of pharmaceutical compounds and nutrition products. Since the polar and hydrophobic components of molecules have substantially different electron populations, Quantum Electrodynamics (QED) shows that these components differentially absorb energy from photons. Coupled with a modulation frequency close to one of the major axes of a given molecule, modulated laser stimulation can be used to increase the homogeneity of a population of proteins or simple amino acid structures. This can be highly advantageous since the metabolic absorption of amino acid structures is moderated in vivo by shape specific enzymes.

If a simple amino acid nutrient is made homogeneous the number of enzymes required to metabolise the nutrient is reduced. Again the cascade effect of cell chemistry means that such a reduction in the complexity of a particular chemical process can dramatically increase the speed of absorption sometimes by several orders of magnitude since the required enzyme population is far more rapidly manufactured. This is of critical importance in many simple amino acid nutrients since they have a limited life before they are broken down by incidental chemical effects before they can deliver the required effect to the target cells.

Under ideal conditions it will be possible to order the folding of a protein to the desired biological form by successive stimulation of suitable resonant frequencies and the differential polar and hydrophobic absorption of photons. Again the application of a suitable modulated beam to a sufficient volume of protein by conventional means would be impossible as result of the scattering of the light. The sparse constructive node beam disclosed in the present application makes the delivery of the required modulation a practical possibility. A suitable array of the disclosed sparse constructive node beams could be arranged on a conveyor passing the proteins or simple amino structures sequentially under the various modulation frequencies designed to favour each of the desired folding steps.

Clearly much research would be required to determine what modulations would be required to produce a desired protein shape and it may be that in practice very few proteins can be usefully manipulated in this way. Such research is not within the scope of this application; rather this application discloses a method and apparatus capable of moderating aspects of the folding process of proteins in a manner that can be applied to a bulk mass for the first time. It is extremely likely that a range of practical protein structures can be generated by this method and it has been shown by experiment that a population of proteins or simple amino structures can be at least made homogeneous which as mentioned above is useful in itself.

In this regard it should be noted that the rotational polarisation of the light source would cause differential absorption of energy depending on; the "handedness" of a given molecular structure. In addition, if the beam is modulated at the resonance of a given structure, it is possible to either enhance the production of one rotation of a molecule versus the other. At slightly higher energy it is possible to cause the destruction by a separate chemical process of one or other rotation by differentiating the temperature and therefore the reactivity of one rotation versus the other. This is a particularly useful application of the method as many drugs and nutrients depend on only one form of the molecule being present.

In this case of course the maximum Feynman path must be very much shorter and so the maximum depth that rotational polarisation effects would occur would be no greater than a few millimetres in a typically scattering medium. Hitherto no simple practical method has existed to purify a population of molecules to one or other rotation. The method disclosed here provides a means of operating on bulk media to generate a homogeneous single rotation population or to allow a chemical process to preferentially destroy one rotation relative to the other in a mixed population of molecules.

The chemical consequences discussed herein of molecular stimulation by sparse constructive node techniques result primarily from the repeated acceptance and release of photons by atoms at the resonant frequency of the local atomic bonds or local structure. There is a secondary effect on certain molecular forms such as tetrahedral which can be induced to spin provided the effective pulse length is sufficiently short.

While the sparse constructive interference beam is the primary thrust of the present application, it is worth noting that the Hamiltonian solution to Maxwell's equations suggest that cancelled light, although carrying no energy in the conventional sense in that it can not interact by conventional Quantum Electrodynamics (QED) processes may have an effect on the permitivity of free space and some theorists suggest an effect on the strong nuclear force. However since it can not scatter by QED effects this has no detrimental affect on the efficiency of the sparse constructive interference modulation and it could be argued that the permitivity and nuclear absorption effect, should it exist, would tend to enhance the efficiency of the modulated frequency coupling to the molecule. It should be noted that the presence of the Hamiltonian effect has never been satisfactorily proven and many theorists discount its existence as a mere mathematical oddity, however we note it here simply to point out that the effect would tend to enhance rather than degrade the benefit of the sparse constructive in interference effect. The apparatus by its nature can therefor be used as a means of delivering such a theoretical modulated Hamiltonian "scalar" wave.

FIGS. 2 to 8 illustrate elements of the foregoing in more detail.

FIG. 2 shows the sparse constructive interference effect from a 1 percent bandwidth cancellation plate of 5 mm aperture. Black represents constructive nodes.

FIG. 3 shows the same sparse constructive interference in a scattering medium showing minimal degradation of the effect and an increased path width of majority destructive interference.

FIGS. 4 and 5 show typical Cell Adhesion Molecules. Both would have two primary resonances a high Q resonance between the main elements at a relatively low frequency and a higher frequency lower Q resonance between the lobes of each element. The molecule in FIG. 4 has a higher frequency resonance between the main elements as it has some backbone structure between the main elements.

FIG. 6 shows a human integrin molecule which will have a single substantial high Q resonance defined by the mass of the two main elements and the compliance of the single backbone structure between the elements. This molecule is extremely easy to resonate sufficiently to moderate reactions and was the first molecule to be successfully manipulated by the method disclosed. This allowed an in vitro demonstration of cell adhesion stimulated by laser stimulation through a sparse constructive node cancellation optical device. "Tracks" of adhered cell chains could be generated in the beam path of the device in a population of cells with substantially reduced expression of the integrin and generally little adhesion in the absence of the beam.

FIG. 7 shows the zinc "fingerlike" structure of the GAG protein in the HIV virus. Again the molecule shows the easily resonated dual element with compliant single backbone bridge. This molecule is much smaller and requires a higher energy and resonant frequency. It was successfully resonated with 470 nm light using the method disclosed. It should be noted that the chemical conditions around a small viral particle are far harder to control or predict and variable results are to be expected. Even so substantial alterations in the processes of the viral coat were observed and the viral penetration of a cell population could be substantially altered.

FIG. 8 shows a typical laser diode spectrum, with a typical cancelled portion of the spectrum and the depth of the modulation that can be induced without causing the nodes to spill outside the cancellation zone and complicate the beat frequency pattern. Different laser designs have different resonant modes and these can be selected to obtain the most useful range for a given application. Bragg gratings can be used to stabilise the laser emission line and expand the modulation amplitude that can be used while keeping the overall frequency shift within the required boundary. Lasers can be pulsed with short duration pulses, which will produce an isolated traverse though the frequency mode of the laser and this can be determined to a high degree of repeatability. If a Bragg grating is used with a pulse laser the resulting frequency modulated pulse will have a very high degree of control. The combination of the short laser pulse and the rapid resulting traverse of the sparse constructive nodes means that a given point in the volume in front of the laser will be exposed to extremely short (sub picosecond) duration pulses. There are several applications for such short pulses and conventional methods for short pulse generation are relatively costly.

What is claimed is:

1. Apparatus for the production of sub picosecond light pulses, the apparatus comprising a laser producing a collimated or near collimated beam, a phase cancellation optical element through which said beam is passed, said phase cancellation optical element being formed by the series combination of a first diffraction grating, a refractive element and a second diffraction grating, whereby a pattern of interference of constructive and destructive nodes is formed in which the diameter of the beam is set to be a sufficiently low multiple of the wavelength of the beat frequency to allow a substantial Fresnel zone to be apparent in the beam.

2. The apparatus according to claim 1 wherein said laser is a pulse laser.

3. The apparatus according to claim 2 wherein the apparatus further comprises a Bragg grating, and wherein said pulse laser produces short duration pulses.

4. Apparatus for the stimulation of molecular resonance by the application of very low intensity electromagnetic radiation, comprising a laser of multiple line cavity resonance consisting of a laser diode with a collimated or near collimated beam, said beam being passed through a phase cancellation optical element having the characteristic of canceling several of the central lines of the laser frequency while leaving the higher and lower frequencies generally uncancelled such that the beat frequency of the passed frequencies forms a pattern of interference of constructive and destructive nodes in which the diameter of the beam is set to be a sufficiently low multiple of the wavelength of the beat frequency to allow a substantial Fresnel zone to be apparent in the beam and in which an aperture is provided to select a portion of the Fresnel zone wherein a substantial majority of destructive nodes are apparent relative to the constructive nodes and in which means are provided to modulate the laser frequency.

5. Apparatus as claimed in claim 1, wherein the laser frequency is varied by adjusting the current on a laser diode.

6. Apparatus as claimed in claim 1 wherein the laser frequency is varied by physical alteration of a second cavity such as a crystal provided to double the primary frequency.

7. Apparatus as claimed in claim 1 wherein the modulation frequency is a harmonic of the beat frequency.

8. Apparatus as claimed in claim 1 wherein the modulation frequency is a harmonic of a specific molecular resonance.

9. Apparatus as claimed in claim 1 wherein the aperture or angle of the beam passage through the cancellation device may be varied consequently varying the beat frequency.

10. Apparatus as claimed in claim 1 wherein the selected portion of the beam may be varied to alter the balance between constructive and destructive nodes.

11. Apparatus as claimed in claim 1 wherein the means for modulating the laser frequency is the consequential mode transition of a laser diode in pulse mode.

12. Apparatus as claimed in claim 11 where the laser diode mode is held within bounds by reflection from a Bragg grating so that the modulation of the Fresnel zone nodes is a consequence of the Fourier transform of the pulse.

13. A method of stimulation of molecular resonance by the application of very low intensity electromagnetic radiation modulated at resonant frequencies of molecules of high Q by use of a laser of multiple line cavity resonance consisting of a laser diode with a collimated or near collimated beam, said beam being passed through a phase cancellation optical element said cancellation device having the characteristic of canceling several of the central lines of the laser frequency while leaving the higher and lower frequencies generally uncancelled such that the beat frequency of the passed frequencies forms a pattern of interference of constructive and destructive nodes, in which method the diameter of the beam is set to be a sufficiently low multiple of the wavelength of the beat frequency to allow a substantial Fresnel zone to be apparent in the beam and in which an aperture is provided to select a portion of the Fresnel zone wherein a substantial majority of destructive nodes are apparent relative to the constructive nodes and in which means are provided to modulate the laser frequency.

* * * * *